(12) United States Patent
Taras et al.

(10) Patent No.: US 9,936,991 B2
(45) Date of Patent: Apr. 10, 2018

(54) BONE FRACTURE TREATMENT APPARATUS AND METHOD

(71) Applicant: Union Surgical, LLC, Moorestown, NJ (US)

(72) Inventors: John S. Taras, Moorestown, NJ (US); John P. Taras, Moorestown, NJ (US); Richard T. Briganti, Philadelphia, PA (US); Nham N. Dinh, Philadelphia, PA (US)

(73) Assignee: UNION SURGICAL, LLC, Moorestown, NJ (US)

( * ) Notice: Subject to any disclaimer, the term of this patent is extended or adjusted under 35 U.S.C. 154(b) by 537 days.

(21) Appl. No.: 14/610,007

(22) Filed: Jan. 30, 2015

(65) Prior Publication Data
US 2016/0220289 A1    Aug. 4, 2016

(51) Int. Cl.
| | | |
|---|---|---|
| *A61B 17/82* | (2006.01) | |
| *A61B 17/80* | (2006.01) | |
| *A61B 17/88* | (2006.01) | |
| A61B 17/56 | (2006.01) | |
| A61B 17/68 | (2006.01) | |

(52) U.S. Cl.
CPC ...... *A61B 17/8085* (2013.01); *A61B 17/8004* (2013.01); *A61B 17/8061* (2013.01); *A61B 17/82* (2013.01); *A61B 17/826* (2013.01); *A61B 17/8863* (2013.01); *A61B 2017/564* (2013.01); *A61B 2017/681* (2013.01)

(58) Field of Classification Search
CPC ... A61B 17/82; A61B 17/826; A61B 17/8004; A61B 2017/681
See application file for complete search history.

(56) References Cited

U.S. PATENT DOCUMENTS

| | | | |
|---|---|---|---|
| 3,710,789 A | | 1/1973 | Ersek |
| 5,035,714 A | | 7/1991 | Willert et al. |
| 5,275,602 A | * | 1/1994 | Shimizu ................. A61B 17/80 606/331 |
| 6,827,743 B2 | | 12/2004 | Eisermann et al. |
| 7,131,995 B2 | | 11/2006 | Biedermann et al. |
| 8,007,498 B2 | | 8/2011 | Mische |
| 8,858,577 B2 | * | 10/2014 | Kubiak ............... A61B 17/1114 606/151 |

(Continued)

OTHER PUBLICATIONS

Closed Treatment of Displaced Middle-Third Fractures of the Clavicle Gives Poor Results, Hill, J.M., et al., Journal of Bone and Joint Surgery, May 1998: 537-539.

*Primary Examiner* — Nicholas Woodall
(74) *Attorney, Agent, or Firm* — Gordon & Jacobson, P.C.

(57) ABSTRACT

A tubular mesh implant is provided for fracture fixation. The implant has a rest length between first and second opposite ends, and a central opening defining a rest inner diameter. The diameter of the central opening is reducible over a bone by elongation of the implant and securable to maintain fracture reduction. A method of setting a fractured bone comprises providing the tubular implant having a rest length and a central opening defining a rest inner diameter, introducing the fractured bone through the central opening in the implant, elongating the implant and reducing the inner diameter about the fractured bone, and securing the first and second ends of the implant to the fractured bone.

12 Claims, 23 Drawing Sheets

(56) References Cited

U.S. PATENT DOCUMENTS

| | | | |
|---|---|---|---|
| 8,906,074 B2* | 12/2014 | Kang | A61B 17/8076 606/283 |
| 2002/0032444 A1* | 3/2002 | Mische | A61B 17/7258 606/63 |
| 2004/0087955 A1* | 5/2004 | Bordi | A61B 17/8085 606/74 |
| 2013/0103166 A1* | 4/2013 | Butler | A61F 2/7812 623/36 |
| 2014/0024885 A1* | 1/2014 | Sudekum | A61F 2/0063 600/37 |

* cited by examiner

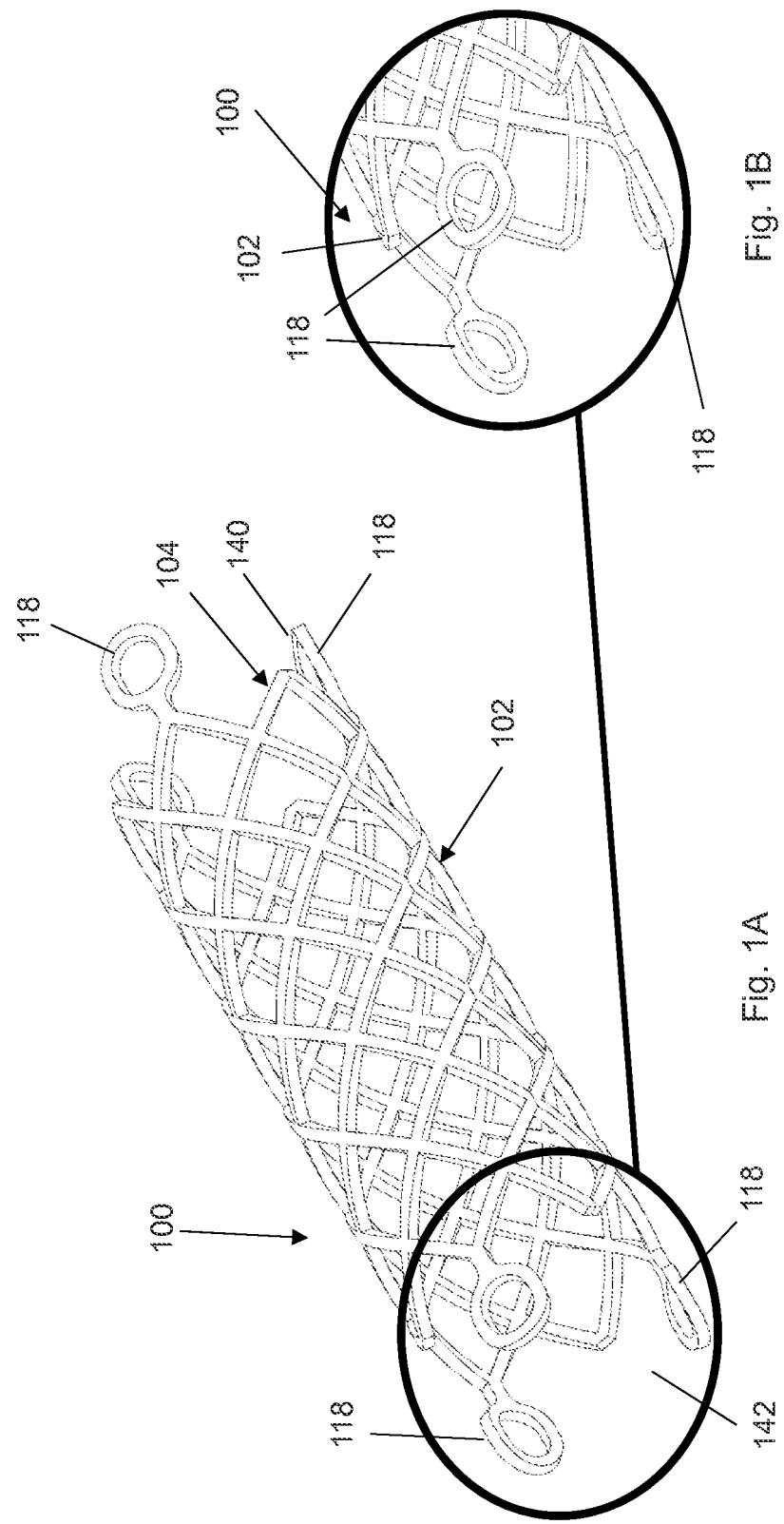

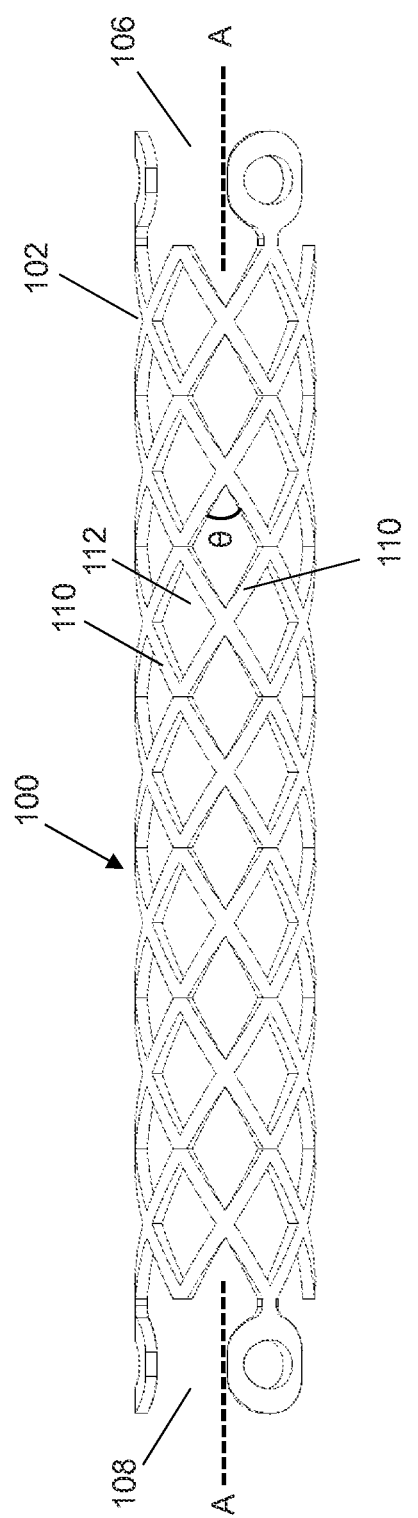

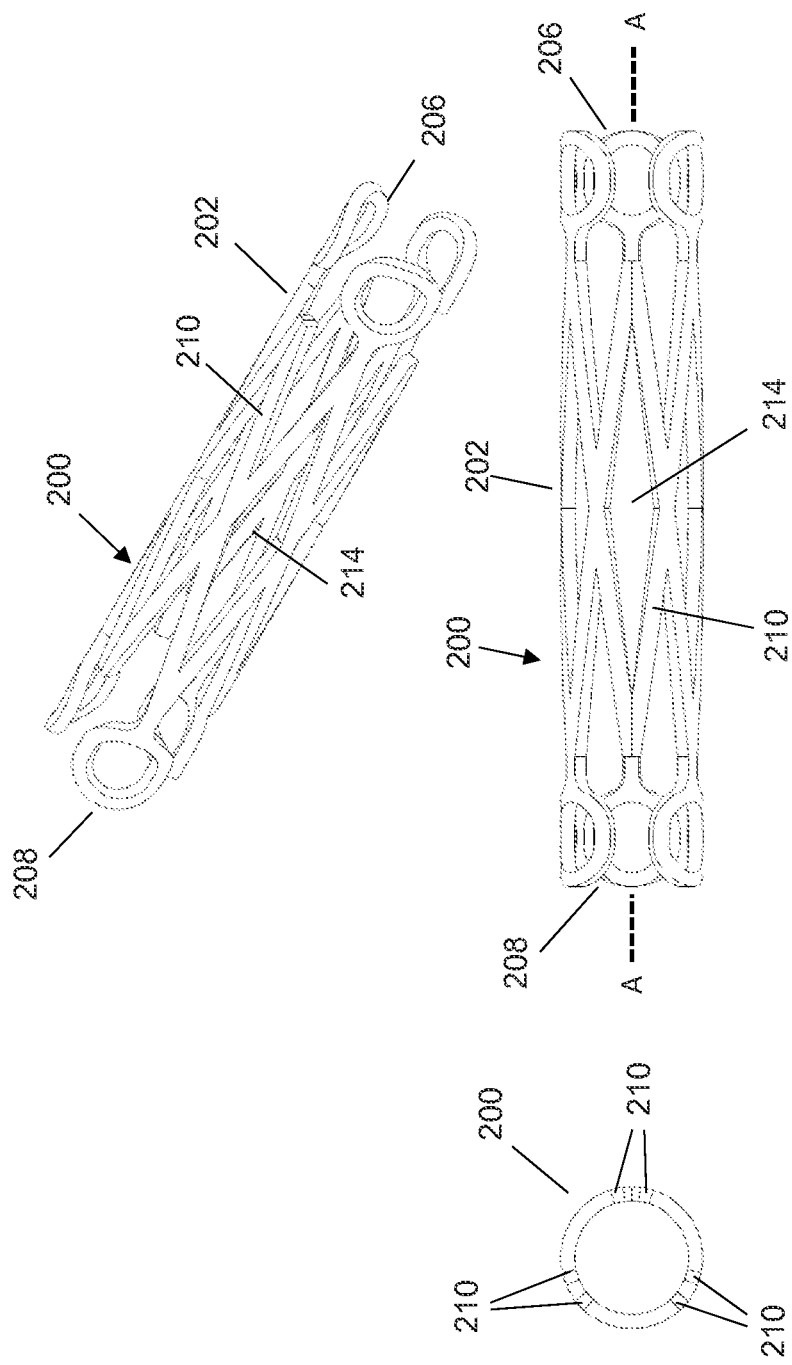

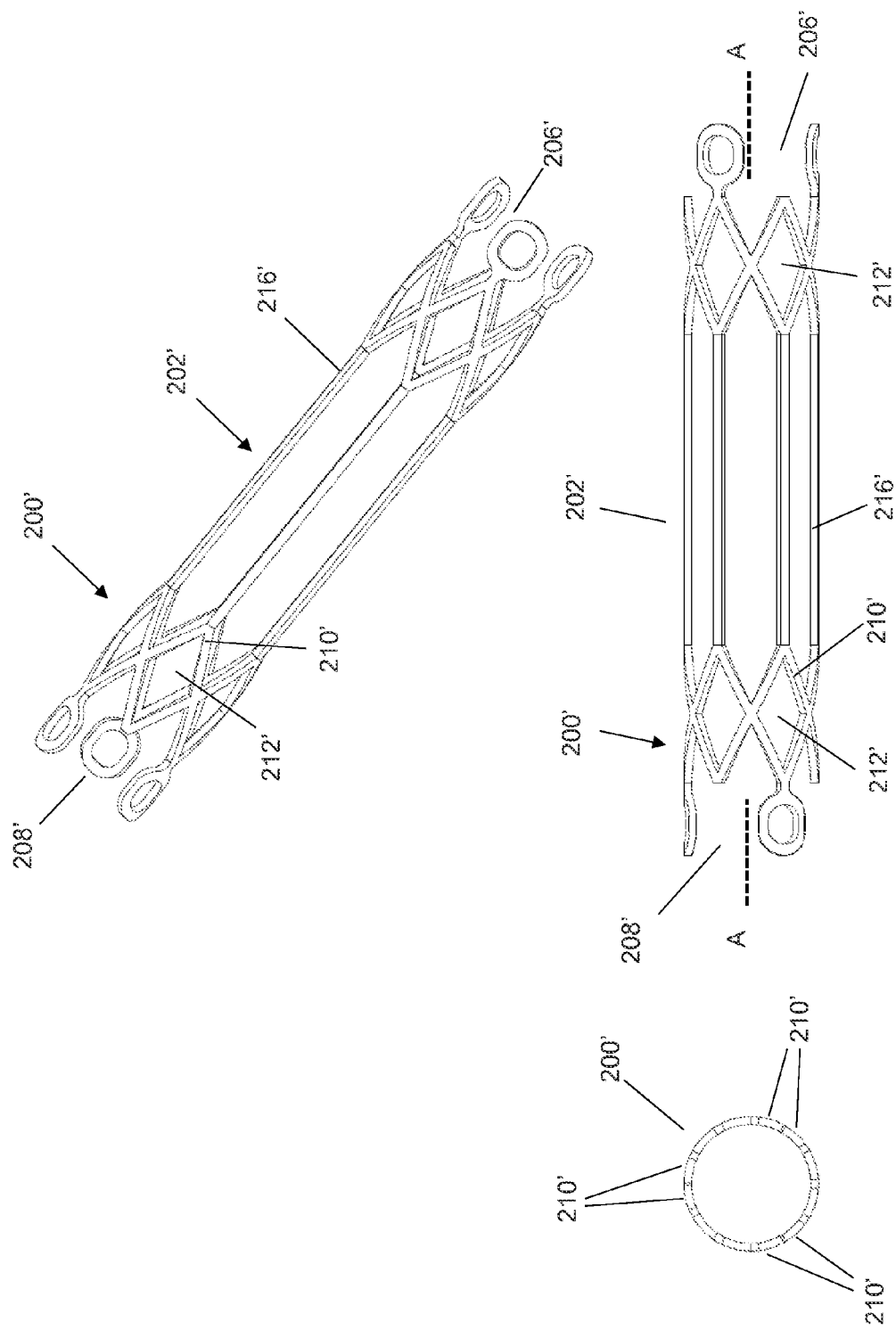

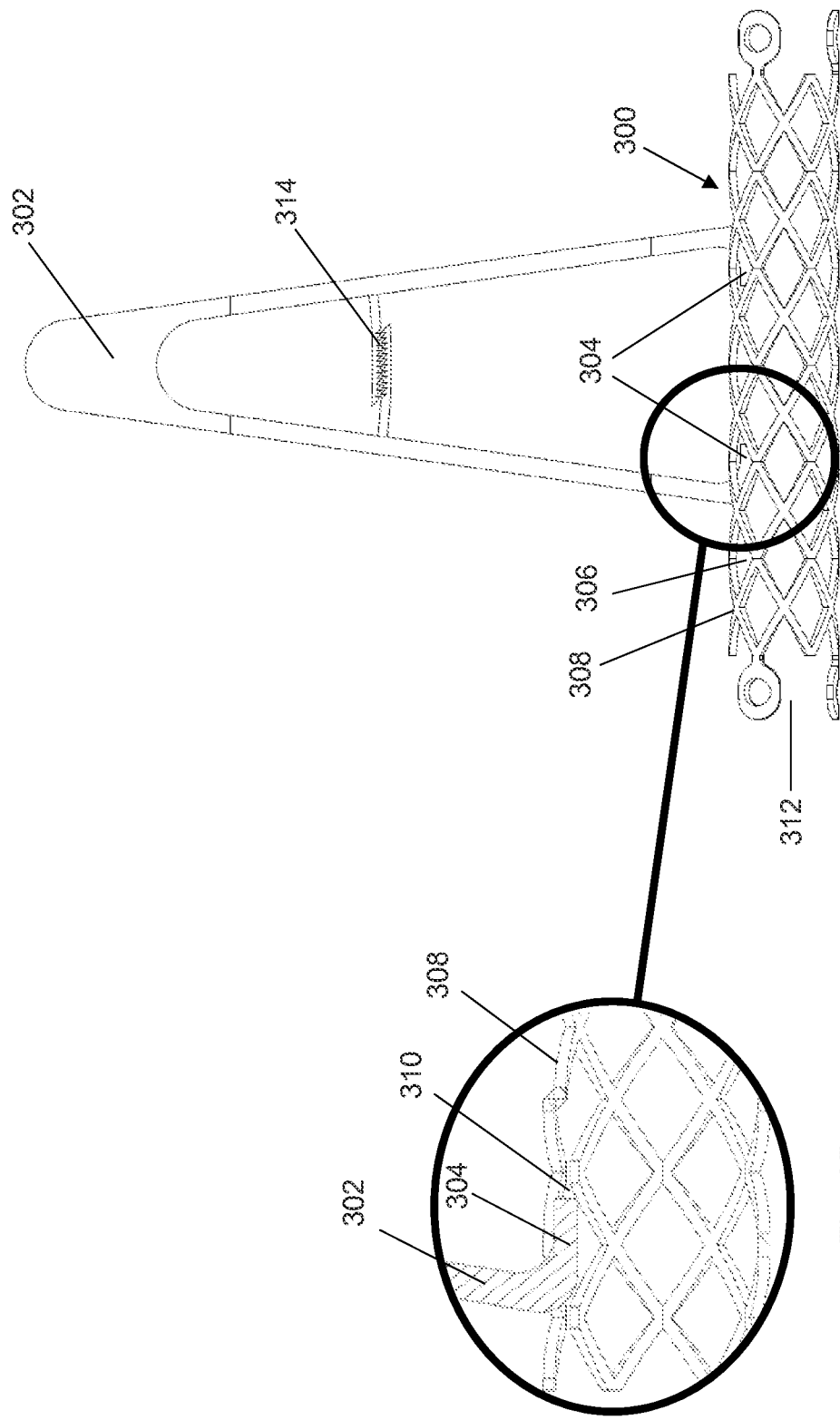

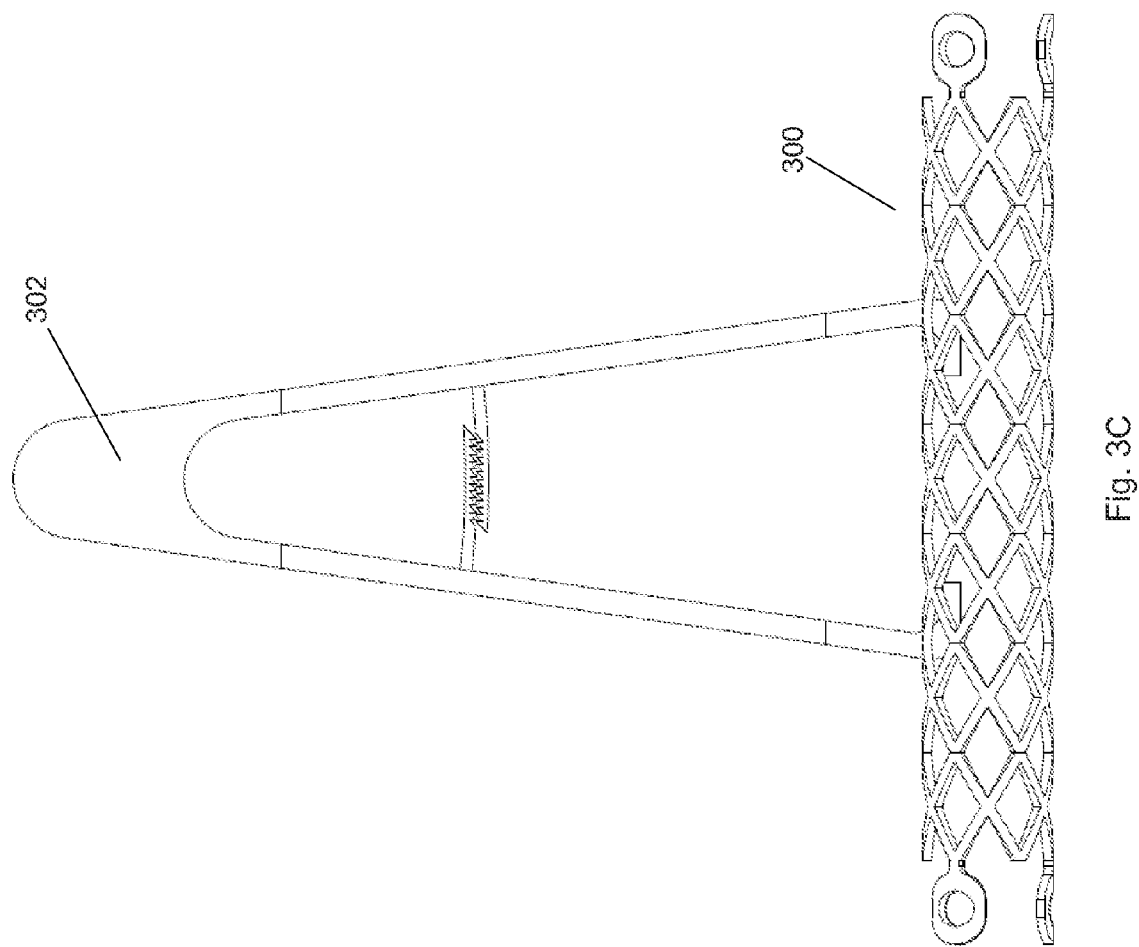

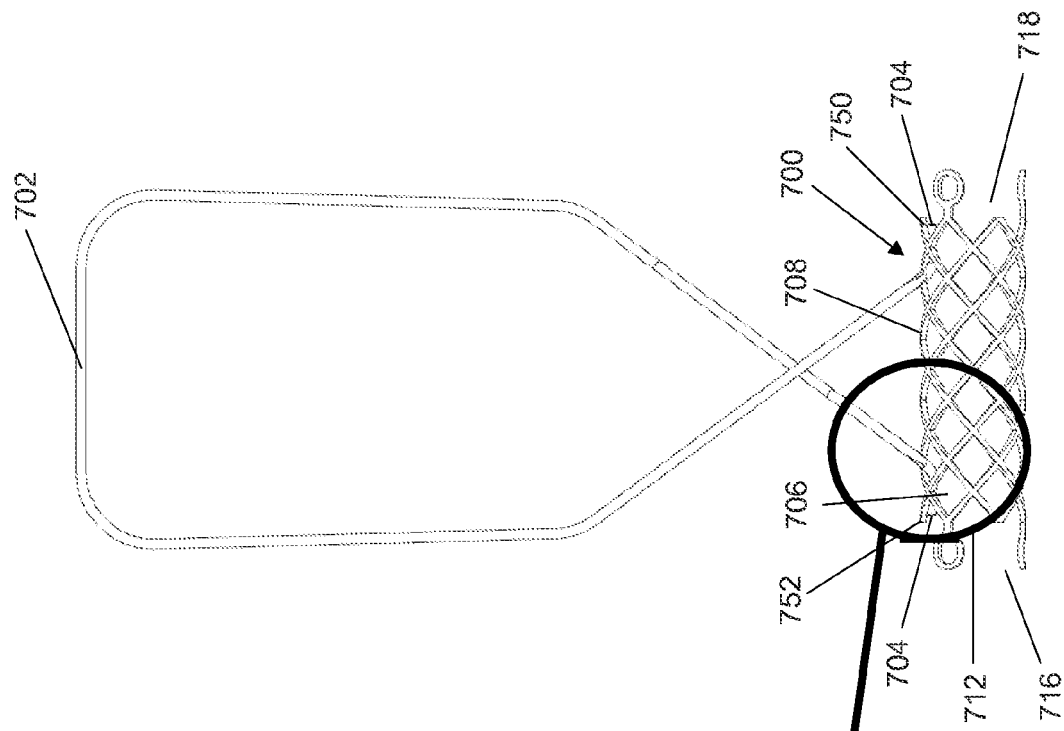
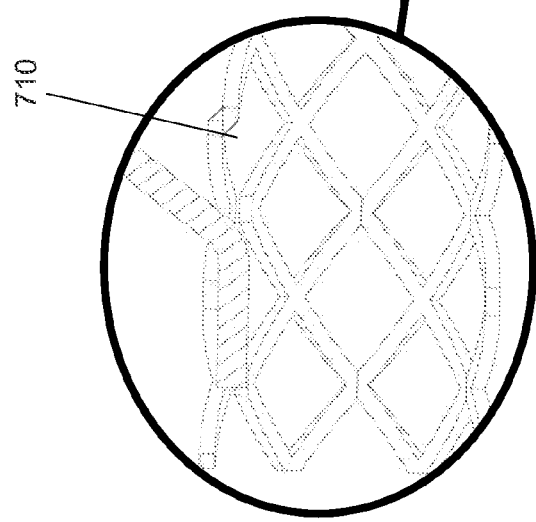

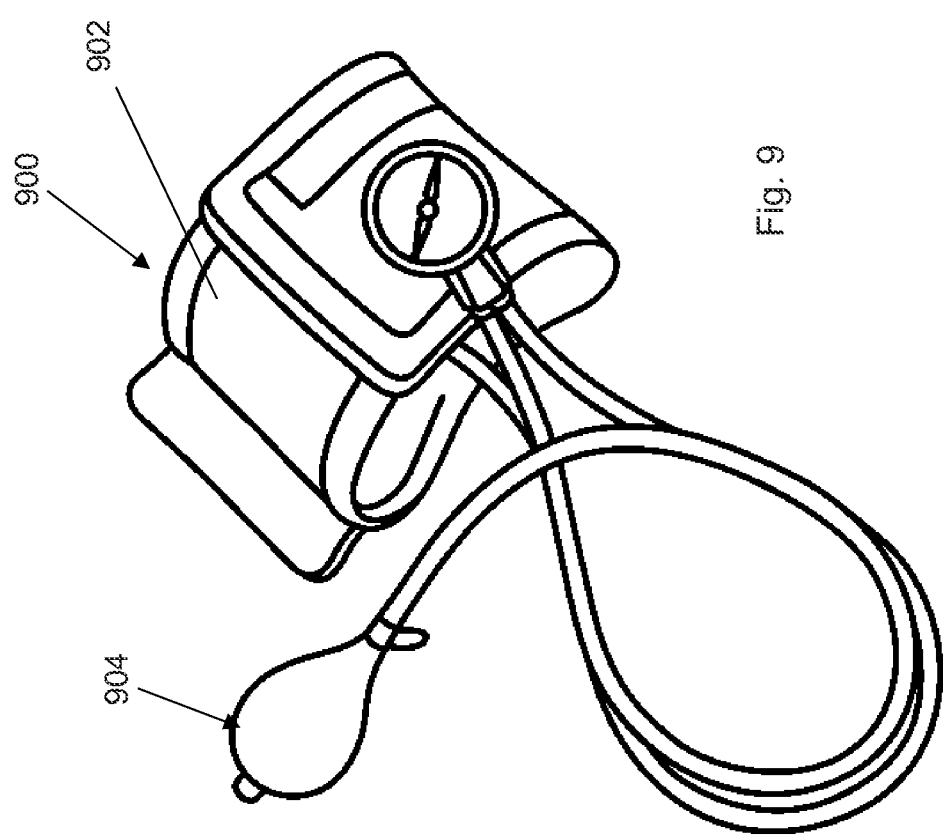

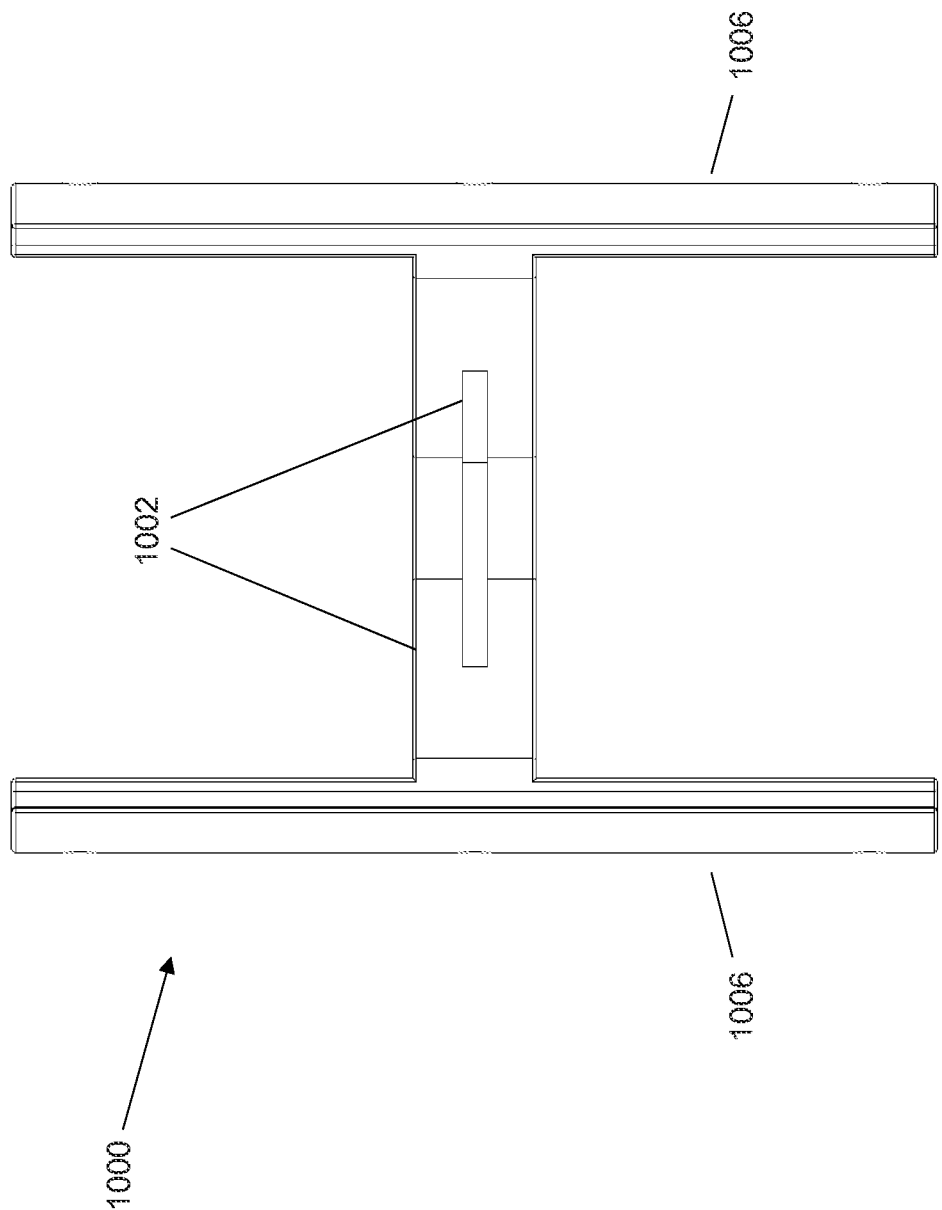

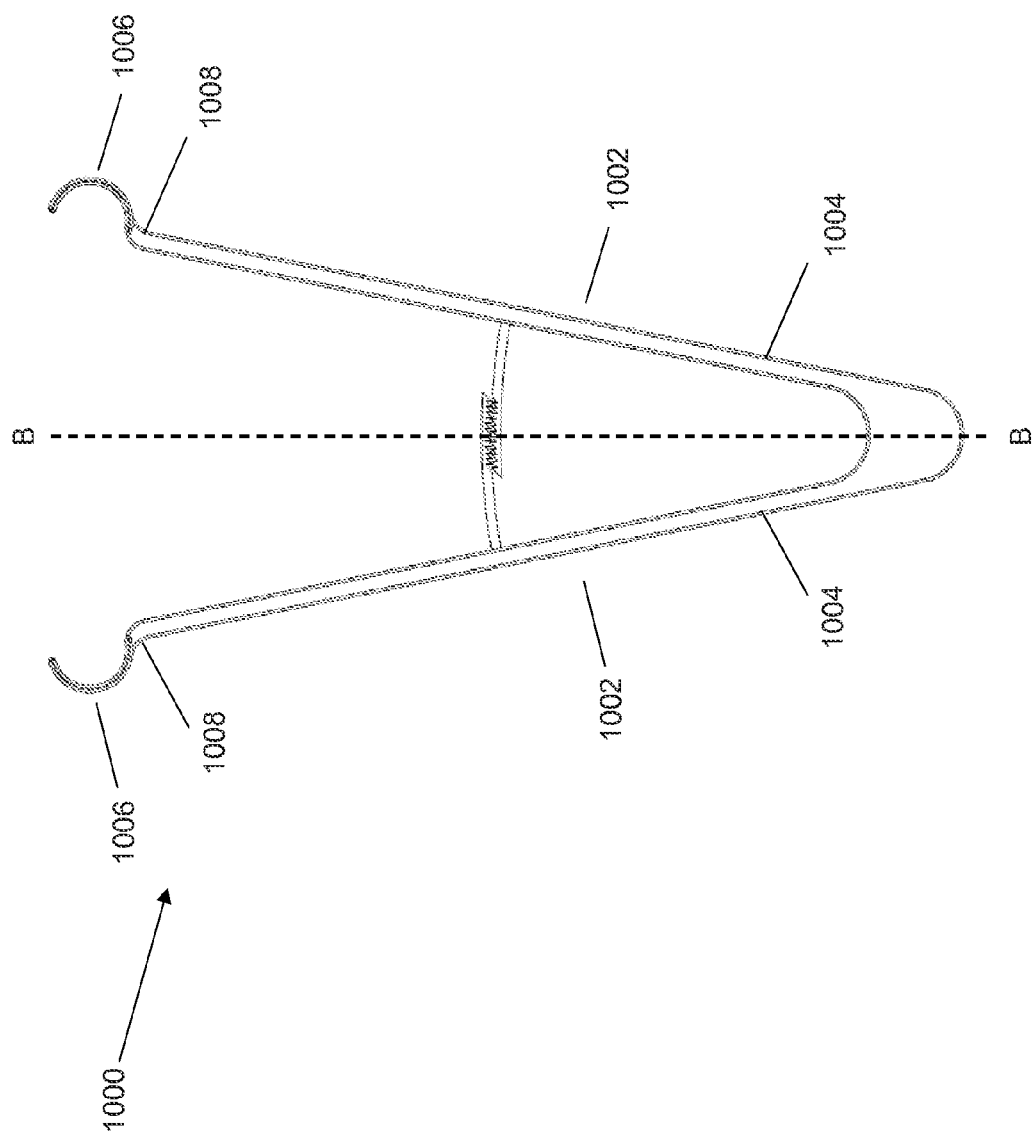

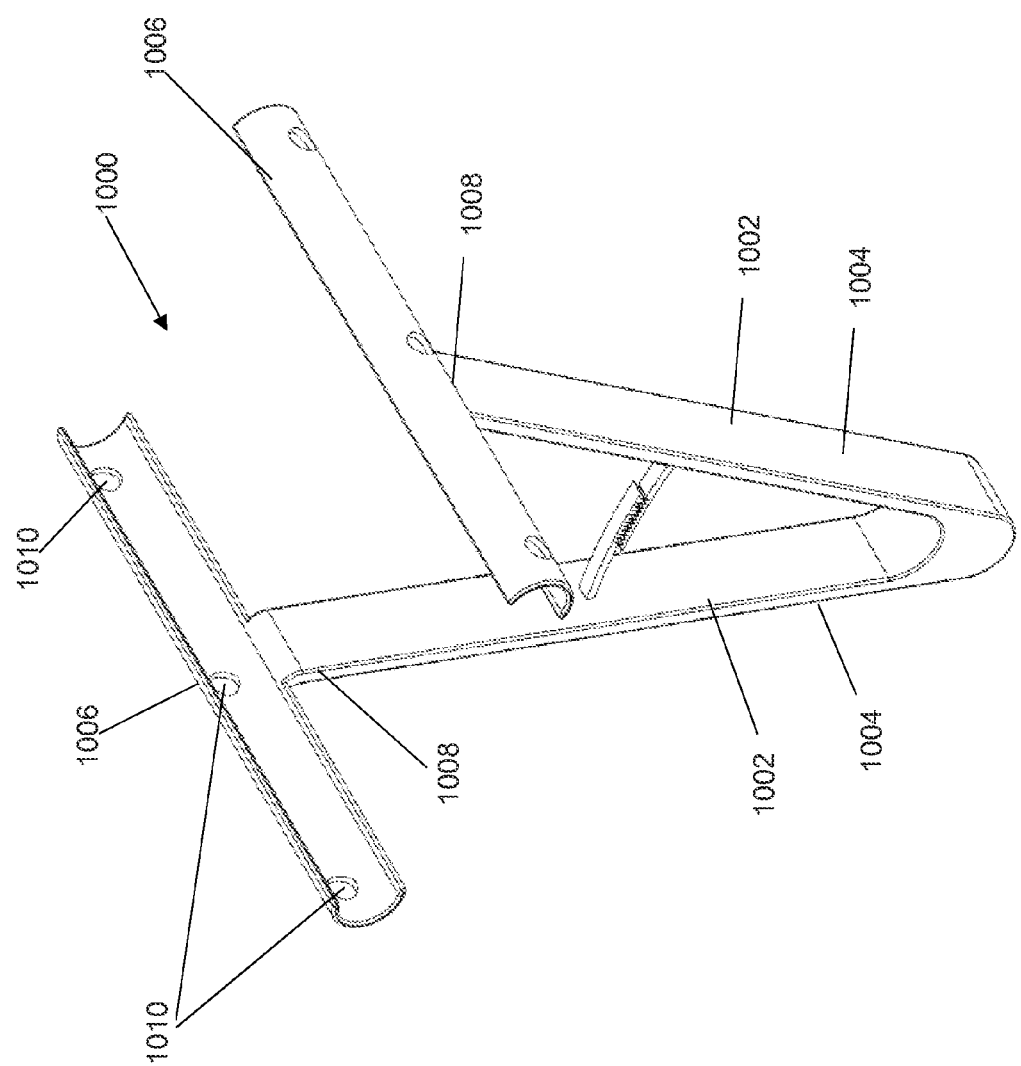

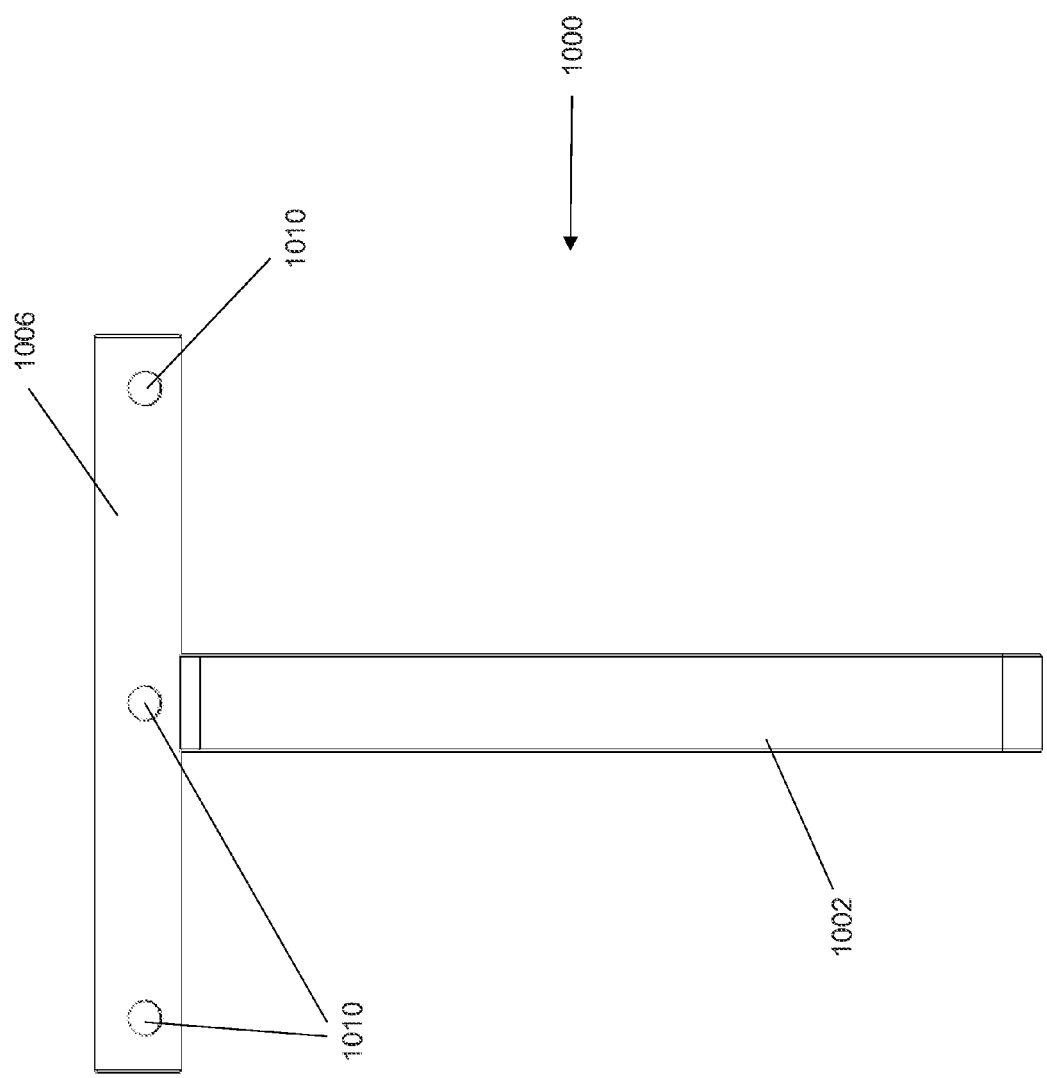

BONE FRACTURE TREATMENT APPARATUS AND METHOD

BACKGROUND

1. Field

The present invention relates generally to the treatment of bone fractures and, more specifically, to implantable devices and methods of their use.

2. State of the Art

Traditionally, orthopedic surgeons have accepted nonoperative treatment as the standard of care for fractured clavicles, likely the result of earlier studies showing unsatisfactory outcomes with operative treatment. However, recent studies show significant risks with nonoperative treatment, including chronic pain, weakness, and a higher nonunion rate. Hill, J. M., et al. "Closed Treatment of Displaced Middle-Third Fractures of the Clavicle Gives Poor Results." *Journal of Bone and Joint Surgery*, May 1998: 537-539. In addition, poor operative results in the past may have been related more to the technique used than the concept of treating these fractures operatively.

Bone screws and hardware used in clavicle fracture surgery may be relatively large and may cause postoperative pain. In addition, such hardware may cause stress shielding that limits transmission of compressive forces through the healed fracture.

SUMMARY

According to a first aspect, a method is provided for setting a fractured bone that comprises providing a tubular implant having a rest length and a central opening defining a rest inner diameter, introducing the fractured bone through the central opening in the implant, elongating the implant and reducing the inner diameter of the implant about the fractured bone, and securing first and second ends of said implant to the fractured bone.

According to one embodiment, the method includes providing an extensible tubular mesh implant having a rest diameter and a rest length. Unless otherwise specified below, the rest diameter refers to the inner diameter of the implant. The tubular mesh implant is constructed for radial and axial extension and compression. The method further includes introducing the first bone portion through a first end of the implant and introducing the second bone portion through a second end of the implant. Also, the method includes applying an axially directed force to the implant to adjust the diameter of the mesh implant from the rest diameter to a first diameter that is larger than the first and second bone portions. In addition, the method includes releasing the axially directed force on the implant with the first and second bones introduced into the implant, so that the implant applies compressive force to at least one of the first and second bone portions.

The tubular implant is extensible and compressible in its axial and radial directions. More particularly, the tubular implant is constructed to change its diameter in response to a change in its axial length. In one embodiment, the diameter of the implant is reduced from an initial rest diameter in response to applying an axially tensile force to the implant in an axial direction along the length of the implant. The reduction in the diameter of the implant allows for an implant with a rest diameter that is larger than the diameter of the bone at the fracture site, so that the implant can be stretched axially over and along the length of the bone at the fracture site and reduced in diameter towards the outer surface of the bone. With the tensile load imparted to the implant and the implant stretched axially along the bone, the ends of the implant are secured to the bone on opposite sides of the fracture site so that the load is transferred to the fracture site to compress the bone about the fracture.

In another embodiment, the inner diameter of the tubular implant is increased from an initial rest diameter in response to applying an axial compressive force to the implant. The implant is constructed so that its diameter decreases towards the initial rest diameter when the compressive force is released. In one embodiment, the initial rest diameter of the implant is smaller than opposing first and second bone portions at a fracture site. An axial compressive force is applied to the implant so that the diameter of the implant is increased from its initial rest diameter to a size that is greater than the diameter of the first and second bone portions so that the first and second bone portions can be introduced into the implant through respective first and second ends of the implant. The first bone portion may be secured to the first end of the implant. Once the first end of the implant is secured, the compressive force on the implant may be released to allow the compressed implant to expand axially and reduce in diameter over the second bone portion until the second end of the implant engages the outer surface of the second bone portion and applies radial compression to the second bone portion. The radial compression retains the second bone portion relative to the implant and, therefore, to the first bone portion. The second end of the implant may be secured to the second bone portion.

It will be appreciated that the implant may engage the second portion of the bone at a compressed length with respect to its rest length. Therefore, the implant may have a tendency to continue to expand further axially toward the rest length even after the diameter of the implant has reduced onto the second bone portion, thereby tending to displace the second bone portion away from the first bone portion at the fracture site. To mitigate this tendency, an external compressive force may be applied to the first and second bone portions to compress the bone portions together while the axially compressive force on the implant is released and the radial compression is applied to the second bone portion by the implant. The external compressive force may be applied by a surgeon. The imparted external compressive force applied to the bone portions may be retained owing to the radial compression applied to the second bone portion by the implant that retains the first and second bone portions in contact with each other. In addition, a tensile load can be applied to the implant while the bone portions are under compression and while the implant is in the process of being secured to at least the same bone portion to facilitate deploying the implant over the bone.

BRIEF DESCRIPTION OF THE DRAWINGS

FIG. 1A is an isometric view of an embodiment of a mesh implant in accordance with an aspect of this disclosure.

FIG. 1B is an exploded view of a first end of the mesh implant shown in FIG. 1A.

FIG. 2A is a side elevation view of the implant shown in FIGS. 1A and 1B extending along axis A-A.

FIG. 2B is a side elevation view of another embodiment of an implant in accordance with an aspect of this disclosure.

FIG. 2C is a side elevation view of another embodiment of an implant in accordance with an aspect of this disclosure.

FIG. 3A is a view of the implant shown in FIG. 1A attached to a clamp.

FIG. 3B is a view of an alternate attachment arrangement between the implant and the clamp shown in FIG. 3A.

FIG. 3C illustrates compressing the implant shown in FIG. 3A with the clamp.

FIG. 3I illustrates additional fasteners between the first and second ends of the implant that secure the implant to the first and second portions of the bone.

FIG. 7A is an isometric view of an embodiment of a mesh implant in accordance with an aspect of this disclosure.

FIG. 7B is an exploded view of a first end of the mesh implant shown in FIG. 7A.

FIG. 9 shows an embodiment of an inflatable device for applying compression to a tubular implant.

FIG. 10A shows a top elevation view of an embodiment of a clamp for applying compression to a tubular implant.

FIG. 10B shows a side elevation view of the clamp of FIG. 10A.

FIG. 10C shows an isometric view of the clamp of FIG. 10A viewed from the side and top.

FIG. 10D shows another side elevation view of the clamp of FIG. 10A from a view rotated ninety degrees about axis B-B with respect to FIG. 10B.

DETAILED DESCRIPTION

Figure 2D:
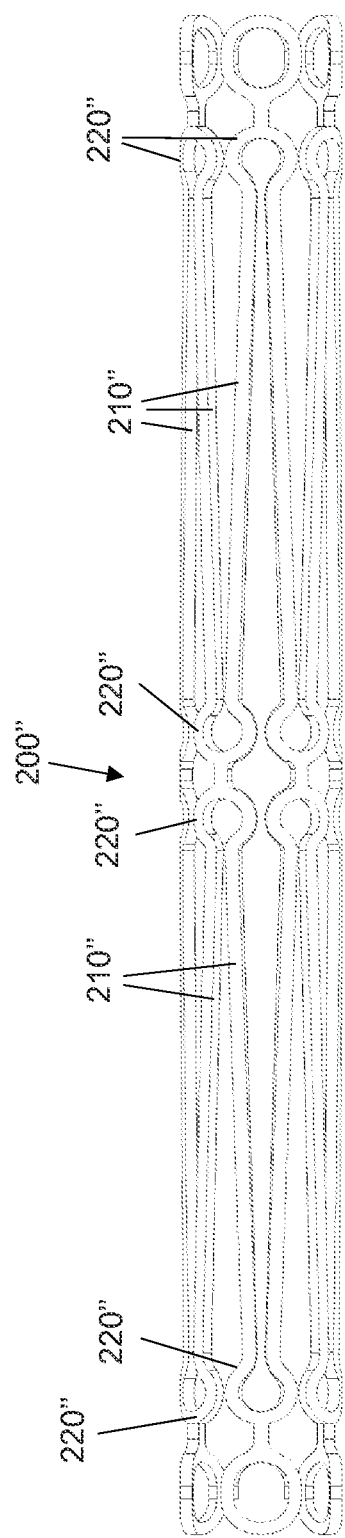
FIG. 2D is a side elevation view of another embodiment of an implant in accordance with an aspect of this disclosure.

FIGS. 1A and 1B show an embodiment of a mesh implant 100 in accordance with an aspect of the present disclosure. In FIGS. 1A and 1B, the implant 100 is shown in what is termed a "rest state", which will be described in greater detail below. The implant 100 is generally formed as a cylindrical tube, a wall 102 of which is preferably formed of a mesh. The wall 102 of the implant 100 defines an interior space 104 in which a first portion 150 and a second portion 152 of a fractured bone 156 (FIG. 3D) are disposed to limit relative movement between the first and second bone portions at a fracture site 156 as the bone 154 heals. To dispose such bone portions 150, 152 in the interior 104 of the implant, the implant 100 has first and second open ends 140, 142, which are constructed to receive the respective bone portions 150, 152, as described in greater detail hereinbelow.

More specifically, the implant 100 is constructed to attach to the bone portions 150, 152 when they are disposed in the interior 104 of the implant 100 to provide rigidity and stability to the bone 154 specifically at the fracture site 156 in order to maintain reduction of the fracture and promote healing. The tubular shape of the implant attached to the outer side of the bone acts to change the moment of inertia of the bone to provide increased strain relief to the bone and resistance to bending and torsion loads during healing.

The implant may be provided with one or more mounting features for securing the implant to the first and second bone portions. For example, as shown in the embodiment shown in FIG. 1B, three screw fixation loops 118 are provided at each of the first and second ends 140, 142 of the implant 100. The screw fixation loops 118 receive bone screws (not shown, e.g., FIG. 3E) therethrough to fix the respective ends 140, 142 of the implant 100 to a bone (e.g., clavicle bone 154, FIG. 3D). In addition to the designated screw loops 118 shown in FIG. 1B, screws may be inserted through the mesh wall 102 or other designated openings at positions on the mesh wall 102 between the ends 140, 142 of the implant 100.

As shown in greater detail in FIG. 2A, the mesh wall 102 of implant 100 has a plurality of crossing, helical struts 110 that extend at opposing angles with respect to a longitudinal axis A-A. The struts 110 intersect and define open cells 112, which in FIG. 2A are diamond shaped. In one embodiment, the included angle $\theta$ between the intersecting struts 110 in the rest state is less than ninety (90) degrees. In FIG. 2A, the cells 112 are regularly spaced longitudinally and circumferentially along the wall 102 of the implant 100.

The number of cells 112 arranged longitudinally along axis A-A may vary based on the length of the implant 100 between its ends 106, 108 and the strain rate that is desired for the implant 100. For example, a greater number of cells may provide a greater resistance to deformation (smaller strain rate) of the implant when subject to the same loads as an implant with relatively fewer cells.

The struts 110 may be formed having cross sections of various shapes. In one embodiment, the cross sections may be square and may have length and width dimensions of about 0.01 inch. In another embodiment, the cross section of the struts 110 may be rounded. For example, the cross section of the struts 110 may be circular and may have a diameter of about 0.01 inch. Other cross sectional shapes of the struts are possible as well without departing from the spirit and scope of the invention.

In other embodiments of an implant, the implant may have a mesh wall with struts that define open cells of a different size than shown above. For example, FIG. 2B shows an embodiment of an implant 200 that has struts 210 that define an open cells 214. Specifically, a wall 202 of implant 200 has struts 210 that define equal sized diamond shaped cells 214 arranged circumferentially between first and second ends 206, 208 of the implant 200.

Referring to FIG. 2D, the intersections of the struts 210" can be formed as a living hinges 220" that reduce the strain on the stent as the struts bend relative to each other when the implant 200" reconfigures from the rest state to a modified diameter. The hinges 220" shown are in the form of a rounded or curved hinge. Other shapes may be provided. Such hinges 220" may be provided to any of the implants described herein.

Also, in yet another embodiment of an implant 200' shown in FIG. 2C, the implant 200' has a mesh wall 202' that includes struts 210' that define equal sized diamond shaped cells 212' arranged circumferentially at the first and second ends 206', 208' of the implant 200' and are spaced between longitudinally extending struts 216' connecting to struts 210'. The longitudinally extending struts 216' extend parallel to each other and to the longitudinal axis A-A through the implant 200'.

In one embodiment, the mesh wall (e.g., 102, 202, 202') of the implant (e.g., 100, 200, 200') is laser cut, such as from a unitary metal tube and may be heat-treated to have a shape-memory or may be super-elastic. The metal tube may be formed of a nickel-titanium alloy that is biocompatible, such as Nitinol. The mesh wall (e.g., 102, 202, 202') may be axially and radially elastic relative to the aforementioned rest state in which the implant is not externally loaded with tensile or compressive forces. The mesh wall (e.g., 102, 202, 202') may be constructed to recoil or otherwise return to the rest state after being axially or radially extended or compressed. For example, the mesh wall (e.g., 102, 202, 202') may be constructed so that axial compression of the implant (e.g., 100, 200, 200'), caused by an axial compressive load applied to the implant, will impart an increase in hoop stress and strain and cause radial expansion of the implant. With respect to implant 100, for example, as the implant 100 radially expands, the angle θ increases.

Also, the mesh wall may be constructed so that axial extension of the implant, caused by an axial tensile load applied to the implant, will reduce hoop stress and strain in the implant and cause radial contraction of the implant. With respect to the implant 100, for example, as the implant 100 axially expands, the angle θ decreases. Thus, the implant can be constructed so that the radial dimension and the axial dimension will change simultaneously, but in opposite relation.

The workflow for using an implant to reduce a bone fracture may be based on the configuration of the implant in its rest state. For example, FIG. 3A shows an embodiment of an implant 300 whose inner diameter can be increased from its rest state by axially compressing the implant 300 using a clamp 302. The clamp 302 has hooks 304 that may be attached to the implant 302 through openings 306 in a mesh wall 308 or in specifically designated pockets (recesses) (310, FIG. 3B) that extend from the mesh wall 308. Such pockets 310 may be useful to dispose the hooks 304 of the clamp 302 outside of the interior 312 of the implant 300 to provide increased clearance for disposing bone portions in the interior of the implant 300. The clamp 302 may be squeezed to compress the implant 300 to thereby cause the inner diameter of the implant 300 to increase. The inner diameter may be increased to accommodate receiving a bone portion in the interior 312 of the implant 300 that has a diameter that is larger than the rest diameter of the implant 300. The clamp 302 has interlocking teeth 314 that can be engaged to retain the clamp 302 and the implant 300 in a compressed state. The interlocking teeth can be disengaged to release the clamp 302 to allow the implant 300 to expand axially while contracting radially, toward the rest state, over bone portions disposed in the interior 312 of the implant 300. If the outer diameter of the bone portions in the interior 312 of the implant is large enough, the implant 300 may engage and lodge itself against the outer surface of the bone portions as the implant recoils, thereby imparting a hoop stress in the implant 300 and a radially directed force to the bone portion. The implant 300 may be attached, such as with fasteners (e.g., bone screws), to bone portions disposed in the interior 312 of the implant 300. In at least one embodiment, in addition to being compressed to accommodate receiving bone portions into the interior 312 of the implant 300, the implant 300 may be stretched axially beyond its rest length prior to being attached to the bone portions to impart an additional compressive load onto the bone portions and across the fracture to facilitate maintaining reduction of the bone fracture.

Also, FIG. 7A shows an embodiment of an implant 700 whose inner diameter can be decreased from its rest state by axially stretching the implant 700 using a clamp 702. The clamp 702 has hooks 704 that may be attached to the implant 700 through openings 706 in a mesh wall 708 or in specifically designated pockets 710 that extend from the mesh wall 708. The pockets 710 may be useful to dispose the hooks 704 of the clamp 702 outside the interior of the implant to provide increased clearance for disposing bone portions in the interior 712 of the implant 700. The clamp 702 is squeezed to increase the distance between the hooks 704 so as to axially stretch the implant 700 to cause the inner diameter to contract. The inner diameter may contract so that the mesh wall 708 interferes with a bone portion disposed in the interior 712 of the implant 700 that has an outer diameter that is smaller than the rest diameter of the implant 700. While the implant is in an at-rest state with a larger diameter, two broken bone portions (e.g., 150, 154, FIG. 3D) may be received through respective opposite ends 716, 718 of the implant 700. The implant 700 is then axially stretched and attached to those bone portions (e.g., 150, 154, FIG. 3D), such as with fasteners (e.g., bone screws), to set the implant 700 with respect to those bone portions. The clamp 702 can be subsequently released and detached from the implant 700 to allow the implant to recoil and transfer the imparted tensile load to the bone portions attached to the implant to impart a compressive load to those bone portions to reduce the fracture.

The implants described herein may be sized according to their rest diameter. Since each implant can be adjusted in diameter and length from its rest diameter, each size of implant may correspond a range of bone diameters that can be accommodated by the respective size of implant. For example, for use on a clavicle bone, an implant designated as a "small" implant may have a 0.256 inch inner diameter in its rest state and may be used to accommodate bones having a diameter of 0.256 to 0.375 inch. Also, an implant designated as a "medium" implant may have a 0.375 inch inner diameter in its rest state and may be used to accommodate bones having a diameter of 0.375 to 0.492 inch. In addition, an implant designated as a "large" implant may have a 0.492 inch inner diameter in its rest state and may be used to accommodate bones having a diameter of 0.492 to 0.614 inch.

Figure 3D:
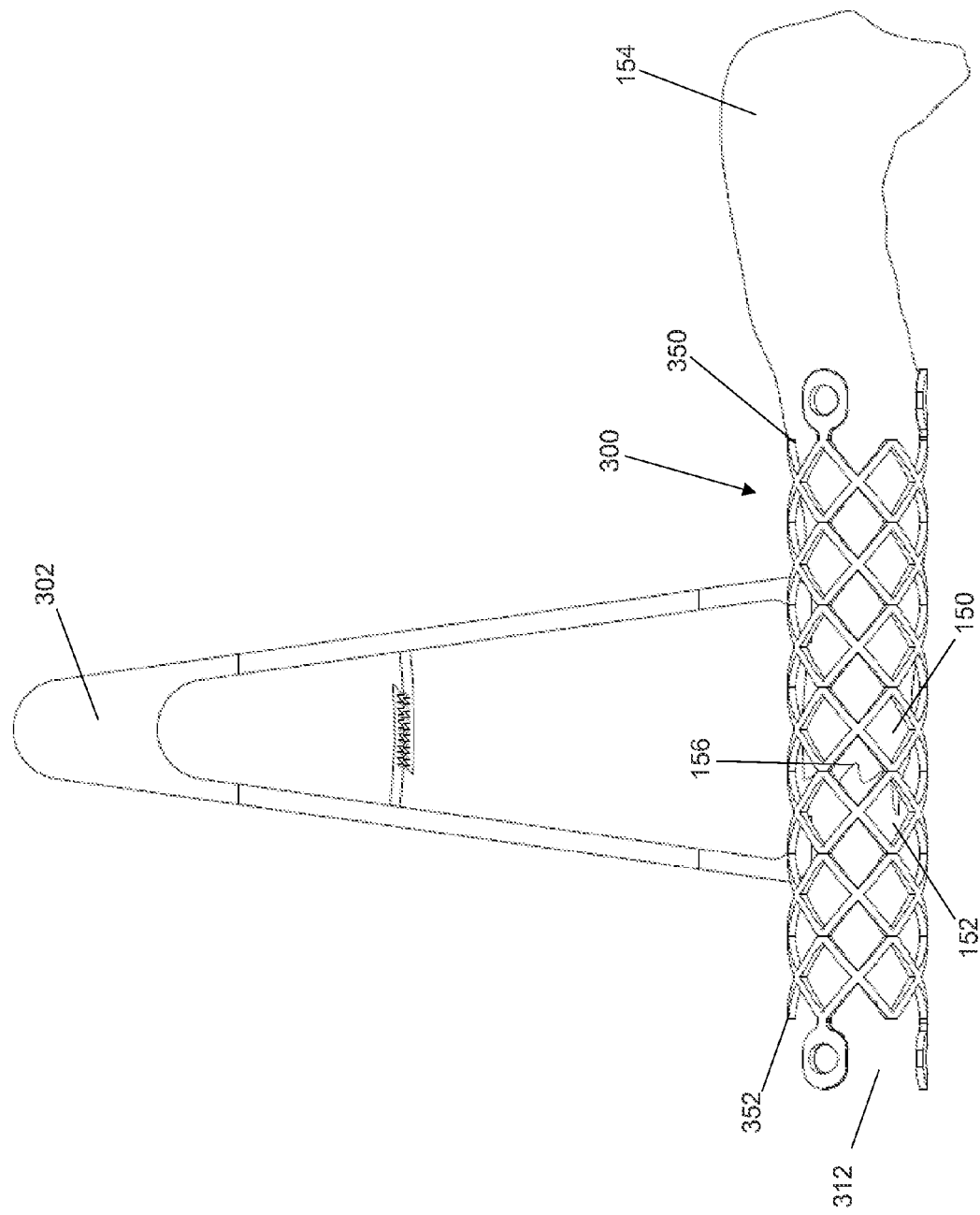
FIG. 3D illustrates the compressed implant of FIG. 3C with portions of a fractured bone disposed in an interior of the implant.
Figure 3E:
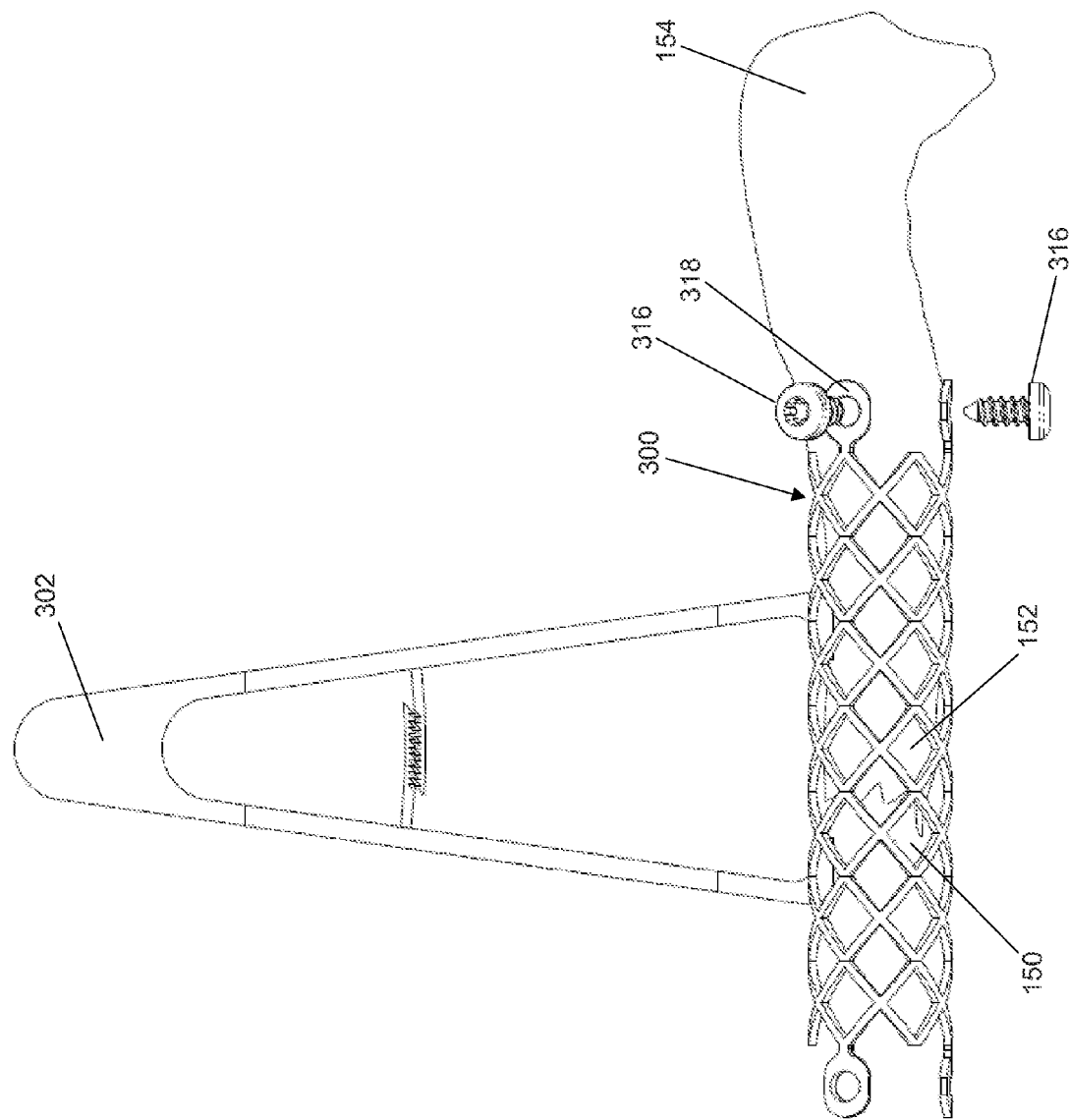
FIG. 3E illustrates positioning of fasteners with respect to mounting features of the implant of FIG. 3C.
Figure 3F:
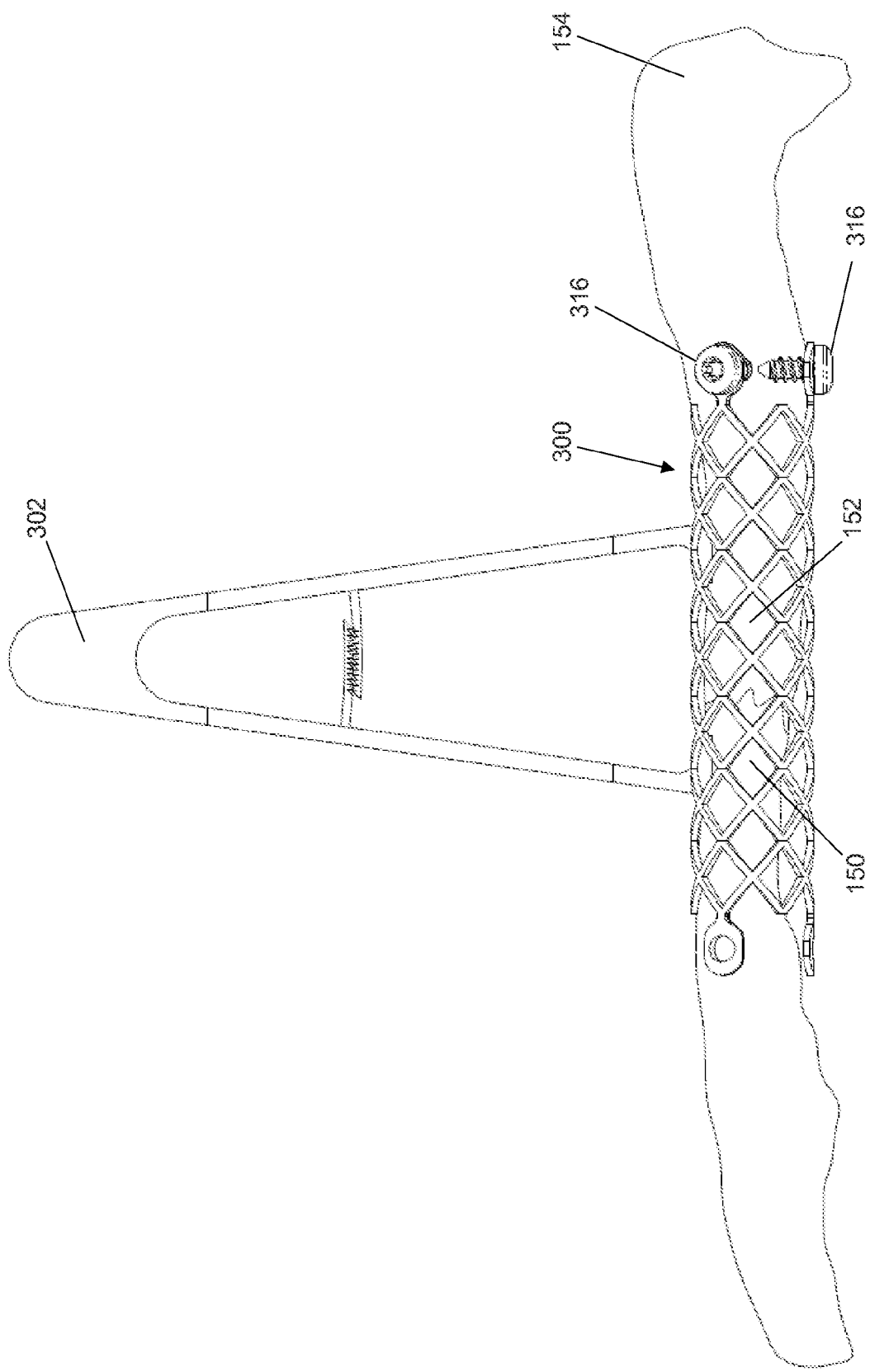
FIG. 3F illustrates the fasteners of FIG. 3E introduced through the mounting features securing the implant to a first bone portion.
Figure 3G:
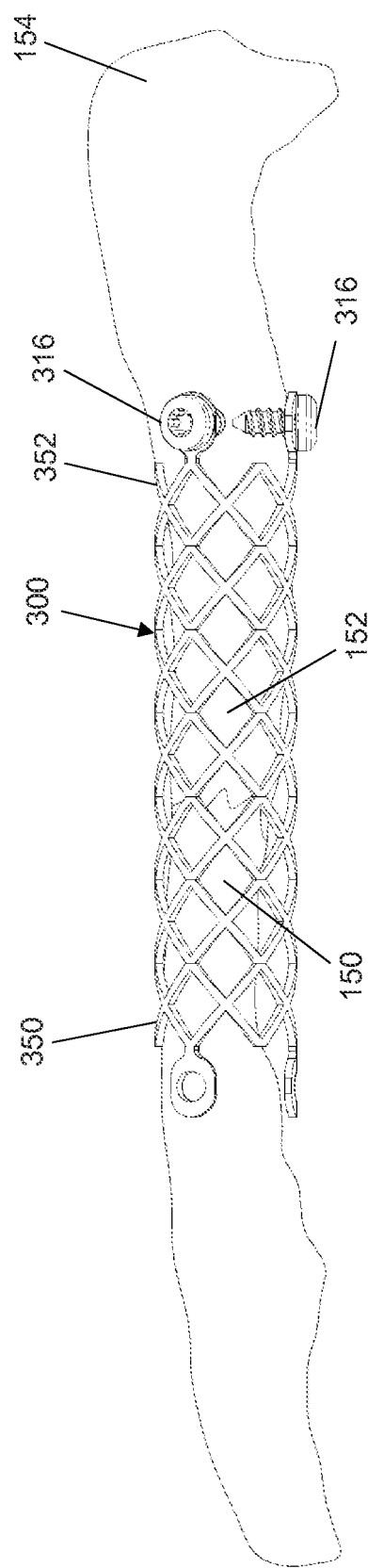
FIG. 3G illustrates the implant secured to the first bone portion and with the clamp of FIG. 3C released and detached from the implant.
Figure 3H:
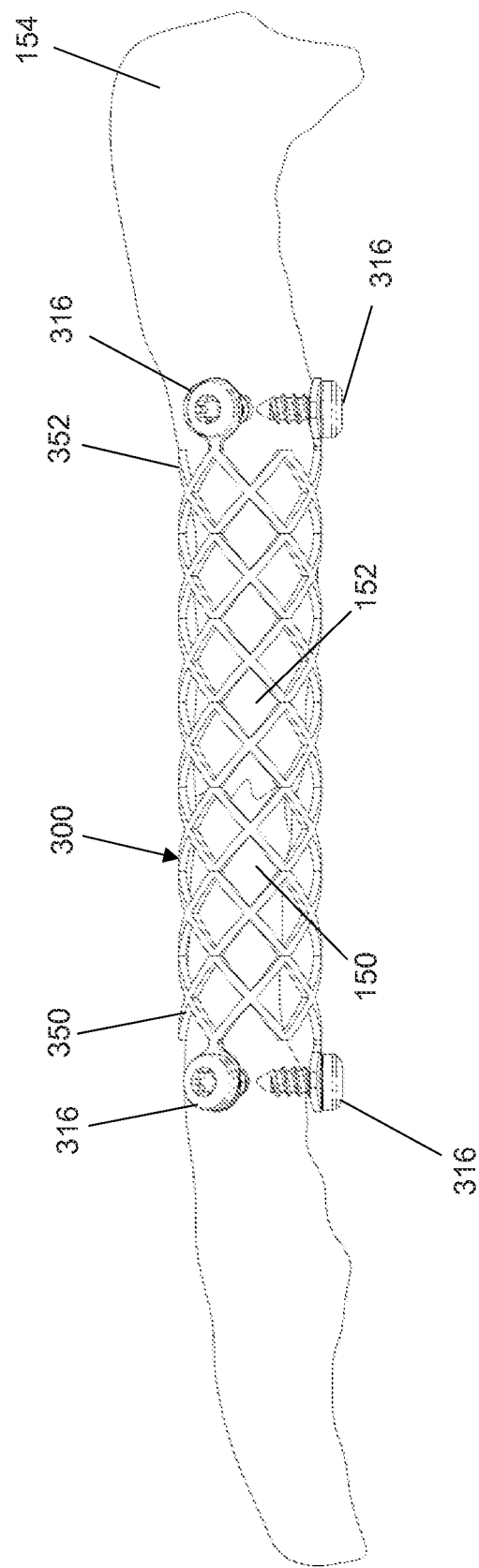
FIG. 3H illustrates the implant secured to both the first bone portion and a second bone portion at respective ends of the implant.
Figure 31:
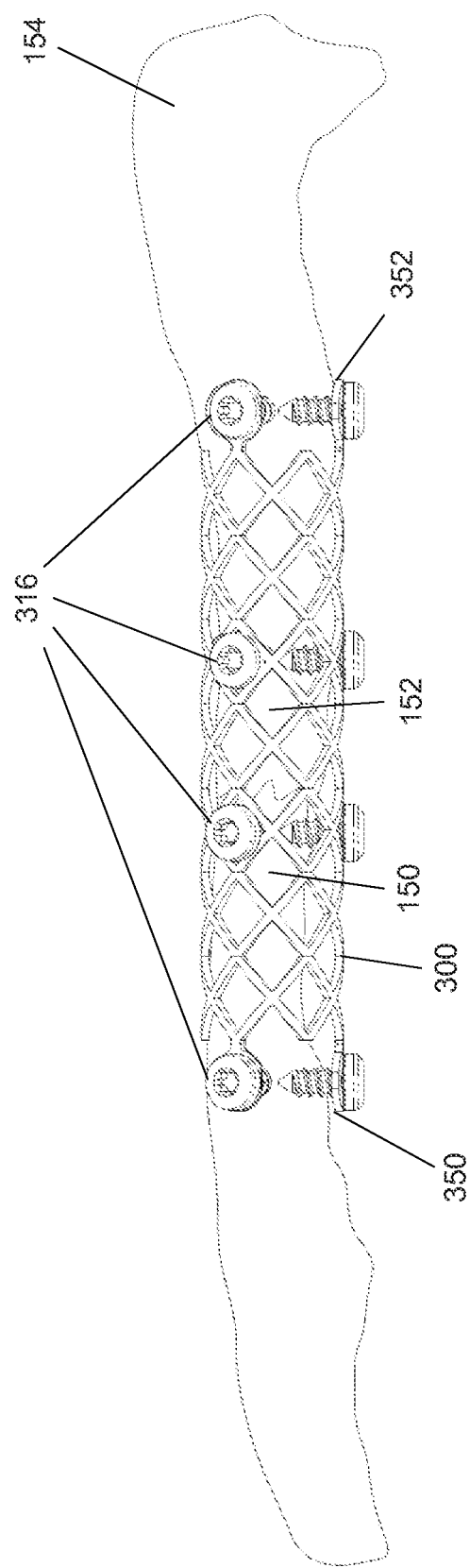
Figure 4:
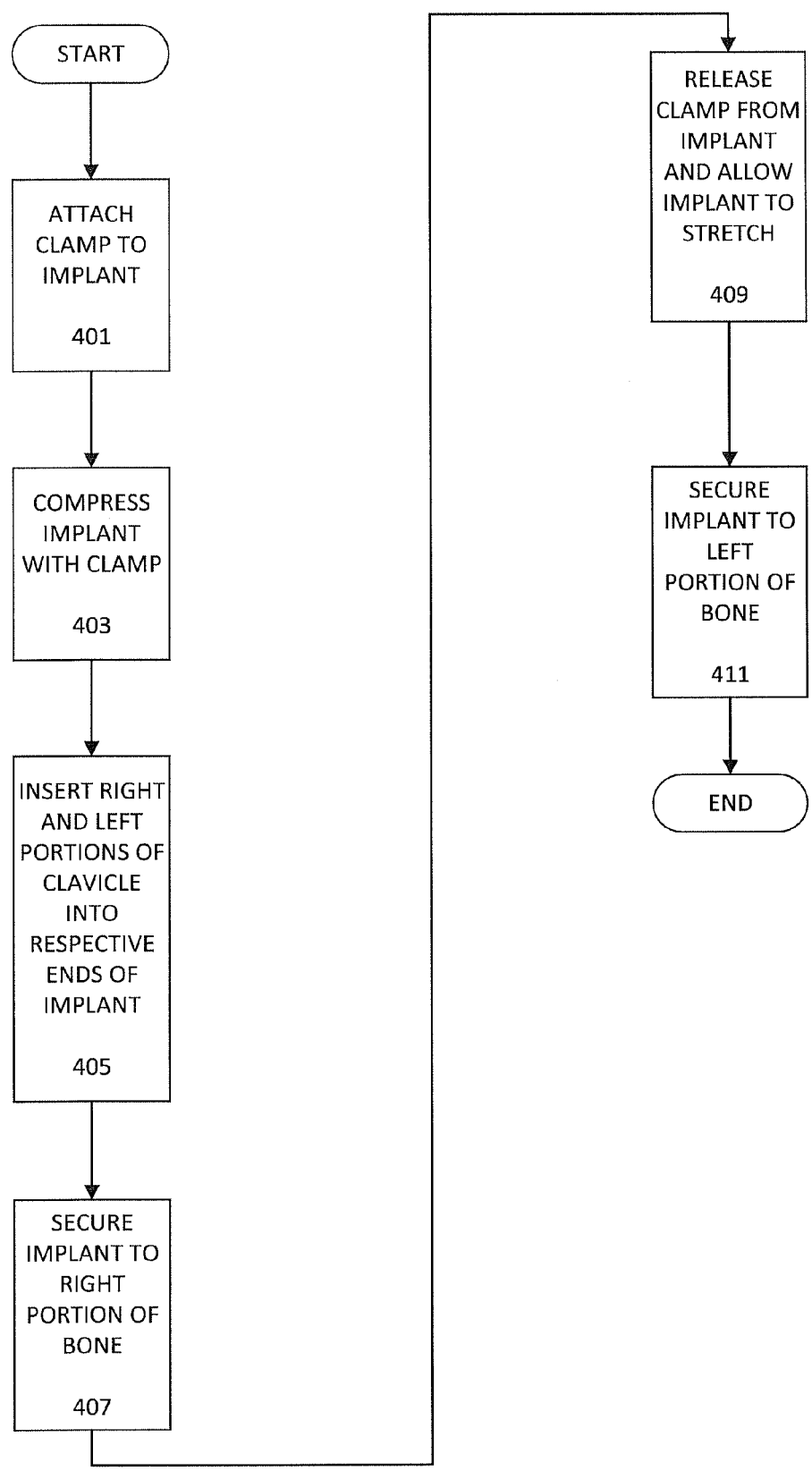
FIG. 4 illustrates an embodiment of a workflow for reducing a bone fracture using an implant.

FIG. 4 illustrates a workflow of using the embodiment of the implant shown in FIG. 3A to reduce a fracture of a clavicle bone. At block 401, the implant 300, in its rest state, is attached to the clamp 302, as shown in FIG. 3A. At block 403, the clamp 302 is squeezed to compress the implant 300, as shown in FIG. 3C. The compression of the implant 300 increases its inner diameter. The implant 300 is compressed at least until the inner diameter of the interior 312 is at least large enough to accommodate the ends of the portions 150, 152 of the broken clavicle bone 154 at the fracture site 156, as shown in FIG. 3D. At block 405, the right portion 150 of the broken clavicle 154 is introduced into the interior 312 of the implant 300 through an open first end 350 of the implant 300 and the left portion 152 of the broken clavicle 154 is introduced into the interior of the implant 300 through an open second end 352 of the implant 300, as shown in FIG. 3D. At block 407, the right portion 150 of the broken clavicle 154 is secured to the implant 300 using screws 316 that are inserted through loops 318 of the implant 300, as shown in FIGS. 3E and 3F. At block 409, the clamp 302 is released to allow the implant 300 to stretch back towards its rest state. As the implant 300 stretches axially, the inner diameter of the interior of the implant 300 contracts. The implant 300 may stretch back to its rest length if its inside diameter does not interfere with the outside of the left portion 152 of the fractured bone 154. Otherwise, the implant 300 stretches towards its rest length until its inner diameter contracts to a position on the left bone portion 152 where it begins to radially compress against the outside of the left bone portion 152, at which point the implant 300 stops stretching. After the second end 352 of the implant 300 stretches as far as it can, as shown in FIG. 3G, at block 411 the second end 352 is secured to the left portion 152 of the fractured clavicle bone 154 with bone screws 316, as shown in FIG. 3H. Optionally, additional bone screws 316 can be inserted through the implant 300 to secure the implant 300 to the portions 150, 152 of the bone 154 at positions between the first and second ends 350, 352 of the implant 300, as shown in FIG. 3I.

Figure 5:
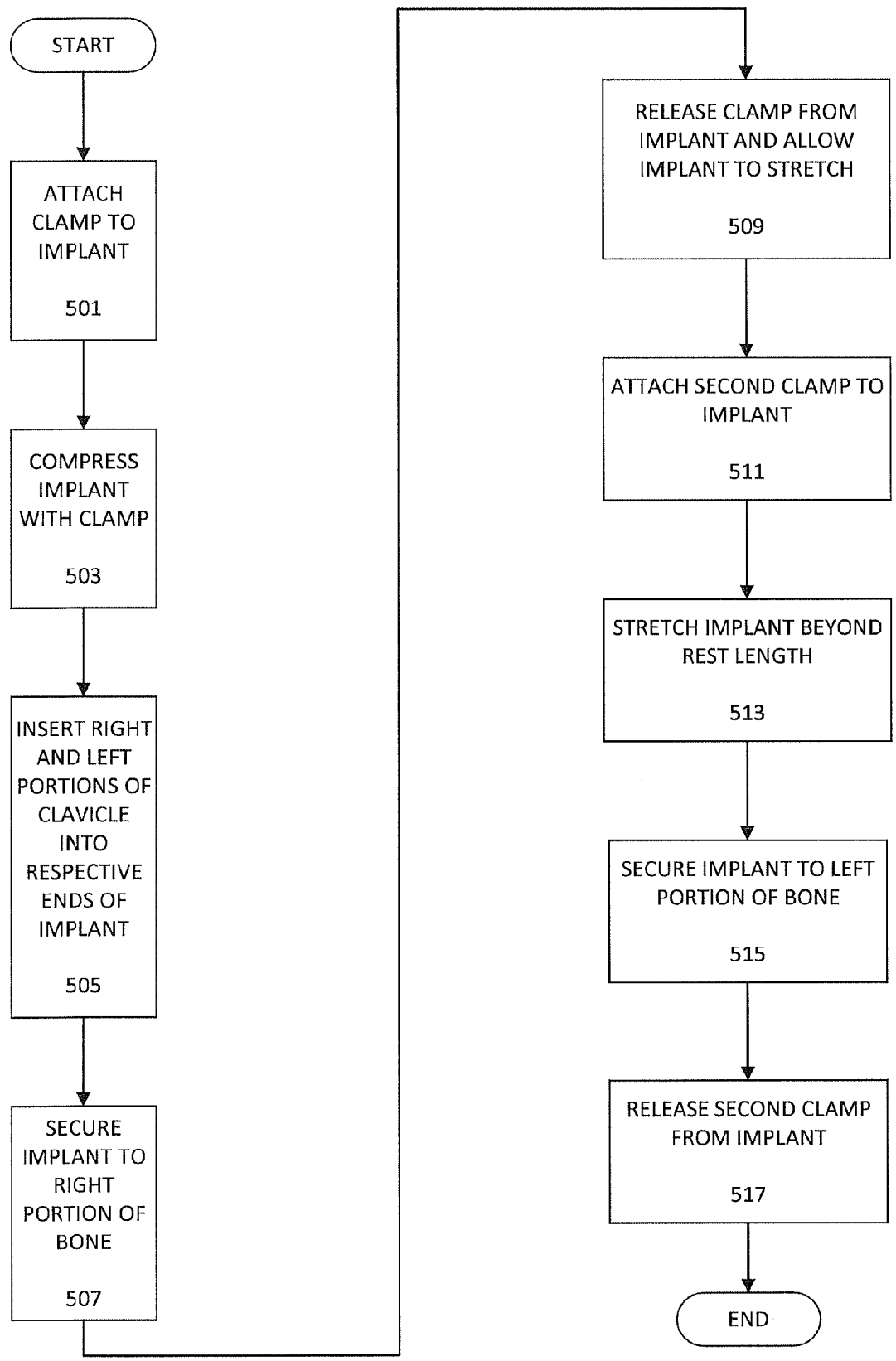
FIG. 5 illustrates another embodiment of a workflow for reducing a bone fracture using an implant.

FIG. 5 shows an alternate workflow to that detailed in FIG. 4. Blocks 501 to 509 correspond to blocks 301 to 309 of the workflow shown in FIG. 3. However, in contrast to the workflow of FIG. 4, in the workflow of FIG. 5, after the clamp 302 is released at block 509 and the implant 300 is allowed to elongate back toward its rest state, a second clamp 702 (FIG. 7) is attached to the implant 300 at block 511 and the implant 300 is stretched axially beyond its rest length at block 513 prior to the implant 300 being secured to the left portion 152 of the broken clavicle bone 154 at block 515. Then, the second clamp 702 is released from the implant 300 at block 517. The additional stretching of the implant 300 beyond the rest length imparts a tensile load to the implant 300. When the implant 300 is secured to the bone portions 150, 152 while it is under tension, the implant 300 transfers the tensile load to the bone portions 150, 152 so that a compressive load is imparted to the bone portions 150, 152 to maintain reduction of the fracture at fracture site 156.

Figure 6:
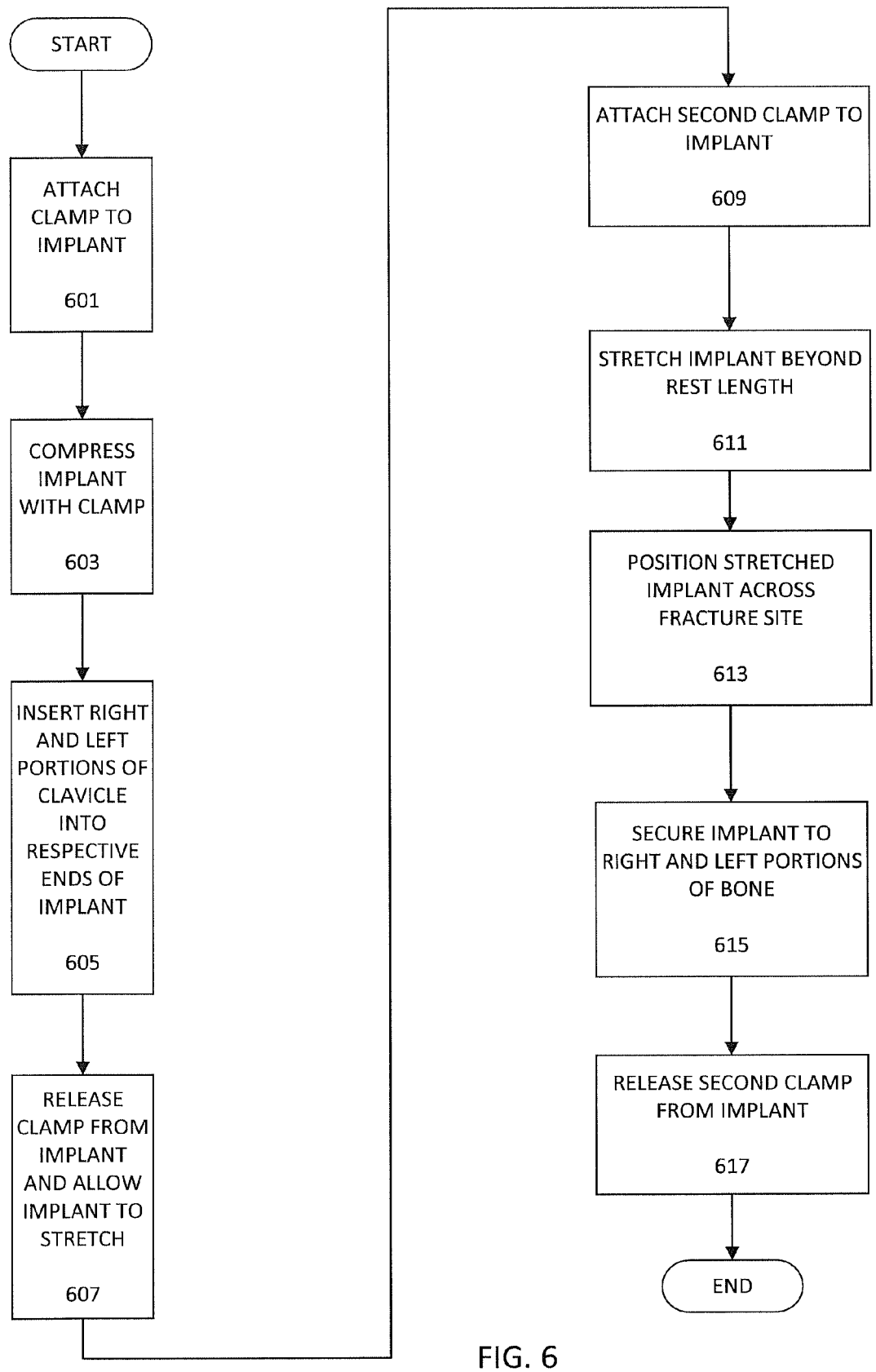
FIG. 6 illustrates another embodiment of a workflow for reducing a bone fracture using an implant.

FIG. 6 shows an alternate workflow to that detailed in FIG. 5. Unlike the workflow of FIG. 5, in the workflow of FIG. 6, the implant 300 is secured to both portions 150, 152 of the fractured bone 154 only after the implant 300 is stretched beyond its rest length and is positioned across the fracture site 156, as discussed in greater detail below. At block 601 a first clamp 302 is attached to the implant 300. At block 603 the implant 300 is compressed. At block 605 the right and left portions (150, 152) of the broken clavicle bone 154 are introduced into the interior 312 of the implant 300 through the first and second ends 350, 352 of the implant 300. At block 607 the first clamp 302 is released so that the implant 300 can stretch on its own along the portions 150, 152 of the bone 154. At block 609 a second clamp 702 (FIG. 7) is attached to the implant 300 and at block 611 the implant 300 is stretched beyond its rest length to impart a tensile load to the implant 300. At block 613 the stretched implant 300 is positioned across the fracture site 156. For example, in one embodiment, the stretched implant 300 is centered over the fracture site 156. At block 615 the implant 156 is secured to the fractured portions 150, 152 of the bone 154. At block 617 the second clamp 702 is released from the implant 300.

Figure 8:
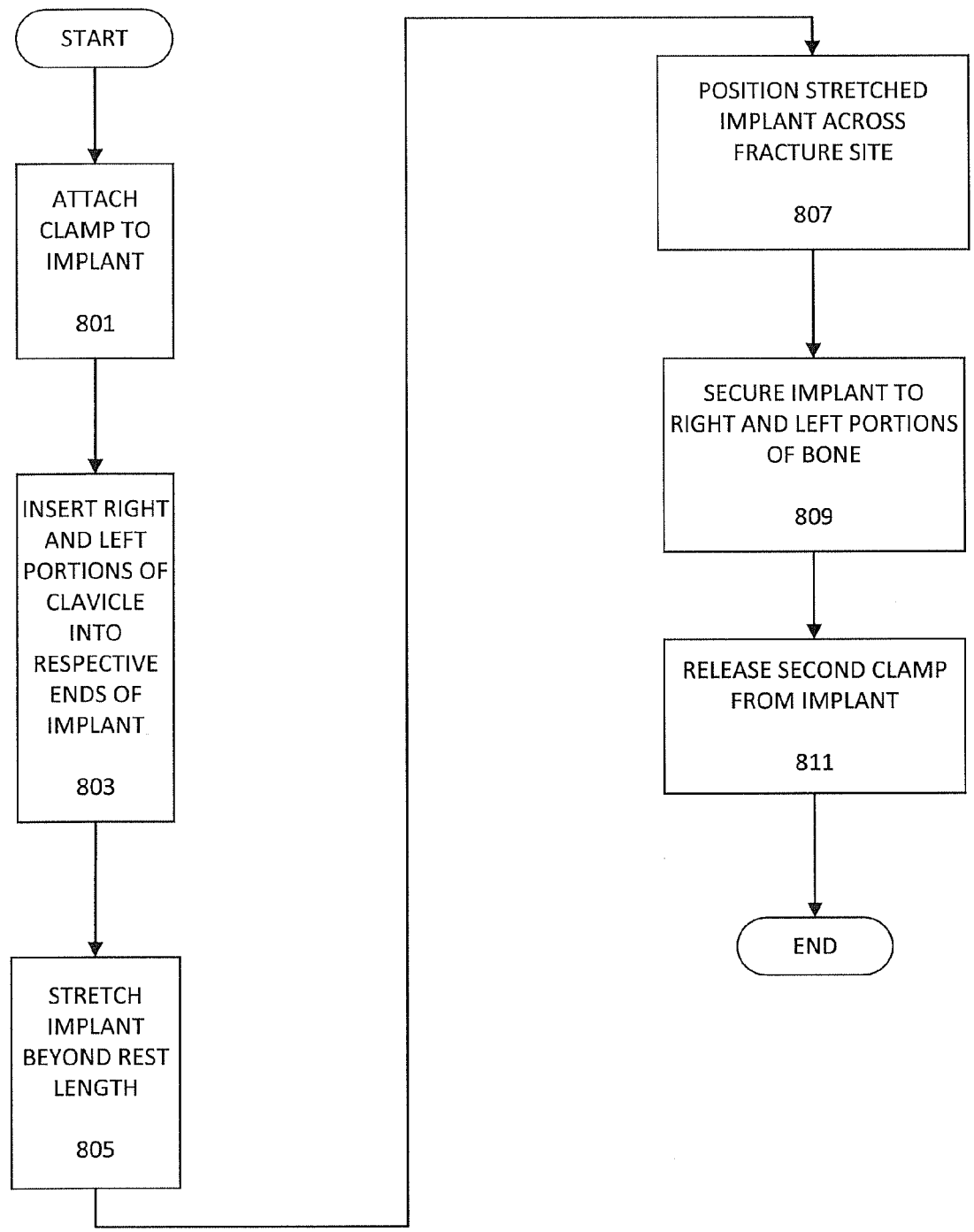
FIG. 8 illustrates an embodiment of a workflow for reducing a bone fracture using the implant shown in FIGS. 7A and 7B.

FIG. 8 illustrates a workflow of using the implant 700 shown in FIG. 7A to maintain reduction of a fracture of the clavicle bone 154. At block 801, the implant 700, in its rest state, is attached to the clamp 702. At block 803, the right portion 150 of the broken clavicle 154 is introduced into the interior 712 of the implant 700 through the open first end 750 of the implant 700 and the left portion 152 of the broken clavicle 154 is introduced into the interior 712 of the implant 700 through the open second end 752 of the implant 700. At block 805, the implant 700 is stretched beyond its rest length. At block 807 the implant 700 is positioned over the fracture site 156. For example, the stretched implant 700 may be centered over the fracture site 156. At block 809 the implant 700 is secured to the right and left portions 150, 152 of the fractured clavicle bone 154. At block 811 the clamp 702 is released from the implant 700. The additional stretching of the implant 700 beyond the rest length imparts a tensile load to the implant 700. When the implant 700 is secured to the bone portions 150, 152, the implant transfers the tensile load to the bone portions 150, 152 so that a compressive load is imparted to those bone portions to promote reduction of the fracture.

The clamps 302, 702 shown respectively in FIGS. 3A and 7 are shown as attaching to discrete points on one side of axis A-A of the implants 300 and 700. Owing to such exemplary illustrated attachments, the tensile and axial forces applied are offset from the central axis A-A of the implant, such that those forces tend to impart a bending moment on the implant. To mitigate the tendency of the implants 300 and 700 to bend or buckle, alternate clamping arrangements are possible that more uniformly apply tensile and compressive forces to the implants. For example, a sleeve, ring, or balloon may used around the circumference of the implants to more uniformly apply axial tension and/or radial compression to the implants. FIG. 9 shows a device 900, which is similar to a miniature blood pressure cuff, has an inflatable cuff 902 that is used to wrap around and compress the implant by inflating the cuff 902 with a squeeze bulb 904. Also, FIGS. 10A to 10D shows a modified clamp 1000 that may be used to compress the implant radially. The clamp 1000 includes arms that are joined together at respective first ends 1004. Both arms 10002 have elongated claws 1006 at respective second ends 1008. The claws each have a curved profile that is constructed to wrap around the outside of an implant. In one embodiment, the claws 1006 have semi-circular profiles, which when compressed against the outside of the implant, apply a radially compressive force to the implant. The claws 1006 define openings 1010 through which bone screws may be introduced to secure the implant to the bones, as described hereinabove.

There have been described and illustrated herein several embodiments of an implant and a method of using the implant to reduce a bone fracture. While particular embodiments of the invention have been described, it is not intended that the invention be limited thereto, as it is intended that the invention be as broad in scope as the art will allow and that the specification be read likewise. Thus, while particular arrangements of the implant and a mesh have been disclosed, it will be appreciated that other arrangements are possible as well. For example, while the implant has been described in at least one embodiment as including a tubular mesh that may be lasercut, in at least one other embodiment, the implant may include a memory metal braid. In addition, while particular types of metals are used for forming the implant have been disclosed, it will be understood that non-metal materials and alloys of metals can be used. For example, and not by way of limitation, stainless steel. Furthermore, while certain procedures of a workflow have been described in an example sequence, it will be understood that the procedures may be combined or performed in a different sequence. It will therefore be appreciated by those skilled in the art that yet other modifications could be made to the provided invention without deviating from its spirit and scope as claimed.

What is claimed is:

1. A method of setting a fractured bone, said method comprising:
   a) providing a tubular implant having a rest length and a central opening defining a rest inner diameter;
   b) introducing the fractured bone through said central opening in said implant;
   c) elongating said implant and reducing the inner diameter about the fractured bone; and
   d) securing first and second ends of said implant to the fractured bone.

2. The method according to claim 1, wherein:
   the rest diameter is smaller than the outer diameter of the bone, and
   said method further comprising:
   e) compressing said implant and increasing the inner diameter from the rest diameter about the fractured bone.

3. The method according to claim 2, further comprising:
   f) releasing the compressed implant to permit said implant to automatically elongate about the bone.

4. The method according to claim 3, wherein:
   said elongating includes elongating the implant after said implant automatically elongates and wherein said elongating elongates the implant to a length that is longer than the rest length.

5. The method according to claim 4, wherein:
   said implant is secured to the bone when the implant is elongated beyond its rest length.

6. The method according to claim 1, wherein:
   the rest diameter is larger than the outer diameter of the bone, and
   wherein elongating the implant causes the implant to contact an outer surface of the bone.

7. The method of claim 6, further comprising:
   f) positioning the elongated implant over a fracture site of the bone.

8. The method according to claim 7, wherein:
   the adjusted implant is centered with respect to the fracture site.

9. The method according to claim 1, further comprising:
   e) applying a compressive force to the bone.

10. A method of setting a fractured bone having a first bone portion and a second bone portion, the method comprising:
    providing an extensible and compressible tubular mesh implant having a rest diameter and a rest length, the tubular mesh implant constructed for radial and axial extension and compression, wherein the rest diameter is larger than the diameters of the first and second bone portions, and
    introducing the first bone portion through a first end of the implant;
    introducing the second bone portion through a second end of the implant;
    applying an axial tensile force to the implant to stretch the implant and adjust the diameter of the mesh implant from the rest diameter to a first diameter that causes the implant to contact at least one of the first and second bone portions;
    while the implant is adjusted, securing the implant to the first and second bone portions; and
    after securing the implant, releasing the axial tensile force to allow the mesh to transfer the force to the first and second bone portions as a compressive force.

11. The method according to claim 10, further comprising:
    positioning the adjusted implant over the first and second bone portions.

12. The method according to claim 11, wherein:
    the adjusted implant is centered with respect to a fracture site between the first and second bone portions.

* * * * *